United States Patent [19]
Luther et al.

[11] Patent Number: 6,015,575
[45] Date of Patent: *Jan. 18, 2000

[54] LIPOSOMOGENIC UV ABSORBERS

[75] Inventors: Helmut Luther, Grenzach-Wyhlen; Dietmar Hüglin, Freiburg; Bernd Herzog, Grenzach-Wyhlen, all of Germany

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/913,531

[22] PCT Filed: Mar. 7, 1996

[86] PCT No.: PCT/EP96/00959

§ 371 Date: Sep. 15, 1997

§ 102(e) Date: Sep. 15, 1997

[87] PCT Pub. No.: WO96/29302

PCT Pub. Date: Sep. 26, 1996

[30] Foreign Application Priority Data

Mar. 17, 1995 [CH] Switzerland ................ 772/95

[51] Int. Cl.$^7$ ............ C07C 219/10; C07C 69/734; C07C 229/12; C07D 251/54
[52] U.S. Cl. ............ 424/450; 424/59; 424/60; 424/70.9
[58] Field of Search ................ 424/450, 59, 60, 424/70.9

[56] References Cited

U.S. PATENT DOCUMENTS 5,605,704 2/1997 Finel et al. ................ 424/450

FOREIGN PATENT DOCUMENTS

| 1246446 | 12/1988 | Canada . |
| 0152379 | 8/1985 | European Pat. Off. . |
| 2 025 957 | 1/1980 | United Kingdom . |
| 2209468 | 5/1989 | United Kingdom . |

OTHER PUBLICATIONS

J. Am. Chem. Soc. (1993), 115(10), 4387–8, XP002007895.
Angewandte Chemie International Ed., vol. 31, 1992, pp. 709–726.
Koch et al. "Photodimerization and photopolymerization of amphiphilic cinnamic acid derivatives in oriented monolayers, vesicles and solution" Makrol. Chem. 187, 1843–1853 (1986).
Watanabe et al, "Studies of Hypolipidemic Agents, I. Synthesis and Hypolipidemic Activities of Alkoxycinnamic Acid Derivatives" J. Med. Chem. 1980, 23, 50–59, 1980.
Chemical Abstracts 85:192401F, Kiguchi et al "p–Alkoxy–α–methylcinnamate esters." 1976.

*Primary Examiner*—Nathan M. Nutter
*Attorney, Agent, or Firm*—Kevin T. Mansfield

[57] ABSTRACT

There are described liposomogenic UV absorbers, comprising a hydrophilic head group (=Z), a spacer (=W), a UV chromophore (Q) having an absorption in the range from 285 to 400 nm and at least one hydrophobic tail group (=A) of the formula (1), in which $A_1$ and $A_2$, independently of one another, are a hydrophobic radical, Q is a UV chromophore, W is an organic radical, $Z_1$ and $Z_2$, independently of one another, are a hydrophilic radical, $n_1$ and $n_2$, independently of one another, are a number from 0 to 4, $n_1=n_2=0$ not being additionally included, p is 1 or 2, q is a number from 0 to 3, $r_1$ is 1 or 2, $r_2$ is 0 or 1, and $s_1$ is a number from 1 to 3. The liposomogenic UV absorbers according to the invention are preferably used as sunscreen agents in cosmetic preparations. They are capable of self-organization into bimolecular layers, and can thereby penetrate into the stratum corneum to a high extent and behave there in an extremely wash-resistant manner.

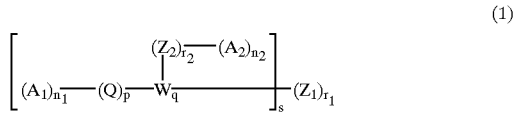

(1)

15 Claims, No Drawings

LIPOSOMOGENIC UV ABSORBERS

This application claims priority under 35 USC 371 of PCT/EP96/000959 filed Mar. 7, 1996.

The present invention relates to liposomogenic UV absorbers, the preparation of these compounds, and their use as sunscreen agents in cosmetic preparations.

It is known that UV rays having a wavelength of 285 to 400 nm can cause or accelerate, in man, skin damage of many different kinds, such as erythemas, accelerated skin ageing, phototoxic and photoallergic reactions etc. For the topical protection of the human skin, chemical compounds in the form of cosmetic preparations are therefore recommended, which are able to prevent the said harmful actions of the UV radiation.

It is furthermore known that the chemical UV absorbers provided in the cosmetic preparations for UV protection themselves only adhere inadequately to or in the skin. It was therefore attempted to eliminate this deficiency by the development of suitable formulations, such as emulsions, gels or oils. Such formulations should permit a longer residence of the UV protective substances on, or in, the outer skin layer. A further, improved possibility of permitting a high penetration of UV absorbers into the stratum corneum and simultaneously a longer residence time of these compounds there consists in applying the corresponding UV absorbers to the skin in liposomal packaging. Such processes are disclosed, for example in WO-92.05761 and WO-93.02659.

Surprisingly, it has now been found that compounds which contain a UV chromophore having an absorption in the range from 285 to 400 nm and specific chemical structural elements which make these compounds capable of self-organization in bimolecular layers, penetrate into the stratum corneum to a high extent and behave there in an extremely wash-resistant manner.

The present invention therefore relates to liposomogenic UV absorbers which comprise a hydrophilic head group (=Z), a spacer (=W), a UV chromophore (Q) having an absorption in the range from 285 to 400 nm and at least one hydrophobic tail group (=A) of the formula $$\left[ (A_1)_{n_1}\text{---}(Q)_{\overline{p}}\text{---}W_{\overline{q}} \begin{array}{c} (Z_2)_{\overline{r_2}}\text{---}(A_2)_{n_2} \\ | \\ \end{array} \right]_{s_1}\text{---}(Z_1)_{r_1} \quad (1)$$

in which
  $A_1$ and $A_2$, independently of one another, are a hydrophobic radical,
  Q is a UV chromophore,
  W is an organic radical,
  $Z_1$ and $Z_2$, independently of one another, are a hydrophilic radical,
  $n_1$ and $n_2$, independently of one another, are a number from 0 to 4, $n_1=n_2=0$ not being additionally included,
  p is 1 or 2,
  q is a number from 0 to 3,
  $r_1$ is 1 or 2,
  $r_2$ is 0 or 1, and
  $s_1$ is a number from 1 to 3.

The compounds according to the invention are synthetic amphiphilic compounds which are able to organize themselves, i.e. in water they spontaneously form a two-dimensional bilayer.

The hydrophobic radicals $A_1$ and $A_2$ are an alkyl, alkoxy, acyl or alkylamino radical, the chains having at least 8 carbon atoms. As alkoxy radicals, $A_1$ and $A_2$ are advantageously the radical of an unsaturated or, preferably, saturated aliphatic monoalcohol having 8 to 22 carbon atoms. The hydrocarbon radical can be branched or preferably straight-chain. $A_1$ and $A_2$ preferably are an alkyl or alkenyl radical having 10 to 14 carbon atoms.

Suitable aliphatic saturated monoalcohols can be natural alcohols, such as lauryl alcohol, myristyl alcohol, cetyl alcohol or stearyl alcohol, and also synthetic alcohols, such as decyl alcohol, $C_{10}$–$C_{13}$oxoalcohol, tridecyl alcohol, isotridecyl alcohol or linear primary alcohols (Alfols) having 10 to 22 carbon atoms. Some representatives of these Alfols are Alfol (10–14), Alfol (12–13) or Alfol (16–18). ("Alfol" is a registered trademark).

Unsaturated aliphatic monoalcohols are, for example, dodecenyl alcohol, hexadecenyl alcohol or oleyl alcohol.

The alcohol radicals can be present individually or in the form of mixtures, such as mixtures of alkyl and/or alkenyl groups which are derived from soya fatty acids, palm kernel fatty acids or tallow oils, of two or more components, preferably individually.

If the radicals $A_1$ and $A_2$ are an alkylamino radical, this is derived from primary or preferably secondary $C_{12}$–$C_{22}$ fatty amines. These amines can be obtained from the corresponding fatty acids by dehydration and subsequent dehydrogenation. Preferably, $A_1$ and $A_2$ as an alkylamino radical are the di-$C_{12}$–$C_{18}$alkylamino radical.

A suitable acyl radical is preferably $C_8$–$C_{22}$alkylcarbonyl; for example octyl-, decyl-, dodecyl-, tridecyl-, hexadecyl- or octadecylcarbonyl.

Preferably, suitable liposomogenic UV absorbers are compounds of the formula (1) in which $n_1$ and $n_2$ are 1 or 2, preferably 2, and the radicals $A_1$ and $A_2$ have the same meaning.

The UV chromophore Q is derived from UV absorbers known per se. Preferably, suitable liposomogenic UV chromophores according to the invention are compounds having structural elements from the class of
  ($Q_1$) cinnamic acid esters,
  ($Q_2$) triazine derivatives,
  ($Q_3$) benzotriazoles,
  ($Q_4$) benzophenones,
  ($Q_5$) p-aminobenzoic acid derivatives, and
  ($Q_6$) benzylidenecamphor.

The cinnamic acid esters $Q_1$ are compounds of the formula $$\text{(2)}$$

in which
  R' is hydrogen, $C_1$–$C_4$alkyl or $C_1$–$C_4$alkoxy,
  $R_1$ is $C_1$–$C_4$alkoxy, preferably methoxy or ethoxy, and
  $R_2$ is hydrogen, $C_1$–$C_4$alkyl or —CN.

Exemplary compounds of the formula (2) are the cinnamic acid methyl or cinnamic acid ethyl ester.

The triazine derivatives $Q_2$ are, for example, hydroxyphenyl-s-triazines of the formula Important s-triazine compounds are those of the formula

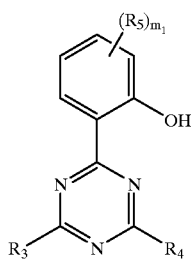

(3)

in which

R$_3$ and R$_4$, independently of one another, are C$_1$–C$_5$alkyl, C$_1$–C$_{18}$alkyl substituted by hydroxyl, C$_1$–C$_5$alkoxy, C$_1$–C$_5$alkylthio, amino or C$_1$–C$_5$mono- or dialkylamino, unsubstituted phenyl or phenyl substituted by chlorine, hydroxyl, C$_1$–C$_{18}$alkyl and/or C$_1$–C$_{18}$alkoxy;

R$_5$ is C$_1$–C$_{18}$alkyl, C$_1$–C$_{18}$alkoxy, halogen, hydroxyl, a radical of the formula

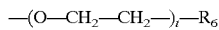

(3a)

or a radical of the formula

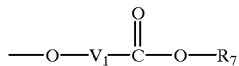

(3b)

R$_7$ is C$_1$–C$_5$alkyl or C$_1$–C$_5$alkoxy-C$_1$–C$_5$alkyl,

V$_1$ is a C$_1$–C$_4$alkylene radical, m$_1$ is 0, 1 or 2, t is 1 to 5, and

R$_6$ is hydrogen or C$_1$–C$_5$alkyl.

If the substituents R$_1$ to R$_6$ are an alkyl group, it can be straight-chain or branched. Examples of such alkyl radicals are methyl, ethyl, n-propyl, isopropyl, n-butyl, isobutyl, sec-butyl, tert-butyl, pentyl, isopentyl, tert-pentyn, n-hexyl, 2-ethylhexyl, n-heptyl, n-octyl, isooctyl, n-nonyl, isononyl, n-dodecyl, heptadecyl or octadecyl.

Examples of C$_1$–C$_{18}$alkoxy or C$_1$–C$_5$alkylthio are, for example, methoxy, ethoxy, propoxy, isopropoxy, butoxy, isobutoxy, sec-butoxy, tert-butoxy, pentoxy, isopentoxy, n-heptyloxy, n-octyloxy, isooctyloxy, n-nonyloxy, isononyloxy, decyloxy, n-dodecyloxy, heptadecyloxy or octadecyloxy or methylthio, ethylthio, propylthio, isopropylthio, butylthio, isobutylthio, sec-butylthio, tert-butylthio, pentylthio, isopentylthio or tert-pentylthio.

Examples of monoalkylamino are monomethyl-, monoethyl-, monopropyl-, monoisopropyl-, monobutyl- or monopentylamino. Examples of dialkylamino which may be mentioned are dimethyl-, methylethyl- or diethylamino.

Halogen is, for example, fluorine, bromine or preferably chlorine.

Important s-triazine compounds are those of the formula

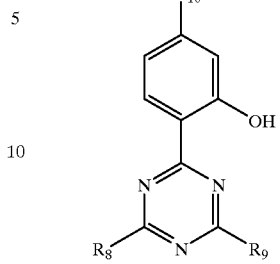

(4)

in which

R$_8$ and R$_9$, independently of one another, are phenyl which is unsubstituted or substituted by C$_1$–C$_5$alkyl and/or C$_1$–C$_5$alkoxy, and R$_{10}$ is hydrogen or C$_1$–C$_5$alkyl.

Further triazine compounds of interest are those of the formula

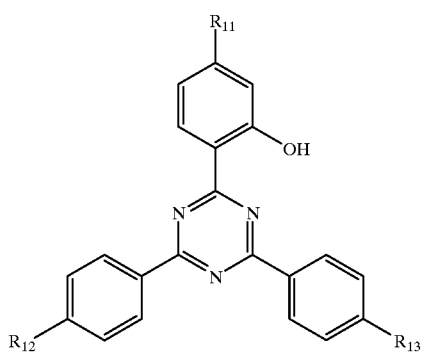

(5)

in which

R$_{11}$ is hydrogen, hydroxyl, C$_1$–C$_{15}$alkyl, C$_1$–C$_{15}$alkoxy or a radical of the formula (3b), and R$_{12}$ and R$_{13}$, independently of one another, are hydrogen or C$_1$–C$_{15}$alkoxy.

Furthermore, hydroxyphenyl-s-triazines of the formula (2) are preferred in which R$_{11}$, R$_{12}$ and R$_{13}$, independently of one another, are C$_5$–C$_{15}$alkoxy, or those compounds in which R$_{11}$ is a radical of the formula (3b) and R$_{12}$ and R$_{13}$ are C$_5$–C$_{15}$alkoxy.

Suitable compounds of the formulae (3), (4) and (5) are, for example:

2-(2'-hydroxy-5'-methylphenyl)-4,6-dimethyl-s-triazine, m.p.=131 C., 2-(2'-hydroxy-3',5'-dimethylphenyl)-4,6-dimethyl-s-triazine, m.p.=177 C., 2-(2'-hydroxy-4',5'-dimethylphenyl)-4,6-dimethyl-s-triazine, λ=349 m, T=48%, 2-(2'-hydroxy-4',5'-dimethylphenyl)-4,6-diethyl-s-triazine, m.p.=98 C., 2-(2'-hydroxy-5'-chlorophenyl)-4,6-dimethyl-s-triazine, m.p.=160 C., 2-(2'-hydroxyphenyl)-4,6-dimethyl-s-triazine, m.p.=133 C., 2-(2'-hydroxy-5'-tert-butylphenyl)-4,6-dimethyl-s-triazine, λ=352 m, T=60%, 2-(2'-hydroxyphenyl)-4,6-didecyl-s-triazine, m.p.=53 C., 2-(2'-hydroxyphenyl)-4,6-dinonyl-s-triazine, m.p.=45 C.,
2-(2'-hydroxyphenyl)-4,6-diheptadecyl-s-triazine, λ=338 m, T=80%,
2-(2'-hydroxyphenyl)-4,6-dipropyl-s-triazine, m.p.=18 to 20 C.,
2-(2'-hydroxyphenyl)-4,6-bis(β-methylmercaptoethyl)-s-triazine, λ=341 m, T=60%,
2-(2'-hydroxyphenyl)-4,6-bis(β-dimethylaminoethyl)-s-triazine, λ=340 m, T=63%,
2-(2'-hydroxyphenyl)-4,6-bis(β-butylaminoethyl)-s-triazine, λ=341 m, T=66%,
2-(2'-hydroxyphenyl)-4,6-di-tert-butyl-s-triazine, λ=338 m, T=68%,
2-(2'-hydroxyphenyl)-4,6-dioctyl-s-triazine, m.p.=40 C.,
2-(2'-hydroxy-4'-methoxyphenyl)-4,6-diphenyl-s-triazine, m.p.=204–205 C.,
2-(2'-hydroxy-4'-ethoxyphenyl)-4,6-diphenyl-s-triazine, m.p.=201–202 C.,
2-(2'-hydroxy-4'-isopropyl)-4,6-diphenyl-s-triazine, m.p.=181–182 C.,
2-(2'-hydroxyphenyl)-4,6-bis(4-methoxyphenyl)-1,3,5-triazine,
2-(2',4'-dihydroxyphenyl)-4,6-bis(4-methoxyphenyl)-1,3,5-triazine,
2-(2'-hydroxy-3'-methylphenyl)-4,6-bis(4-methoxyphenyl)-1,3,5-triazine,
2-(2',3'-dihydroxyphenyl)-4,6-bis(4-methoxyphenyl)-1,3,5-triazine,
2-(2'-hydroxy-5'-chlorophenyl)-4,6-bis(4-methoxyphenyl)-1,3,5-triazine,
2-(2'-hydroxy-4-methoxyphenyl)-4,6-bis(4-methoxyphenyl)-1,3,5-triazine,
2-(2',4'-dihydroxyphenyl)-4,6-bis(4-methoxyphenyl)-1,3,5-triazine,
2-(2'-hydroxy-4-hexyloxyphenyl)-4,6-bis(4-methoxyphenyl)-1,3,5-triazine,
2-(2'-hydroxy-4-hexyloxyphenyl)-4,6-bis(3-methoxyphenyl)-1,3,5-triazine,
2-(2-hydroxy-4-methoxyphenyl)-4-(4-methoxyphenyl)-6-phenyl-1,3,5-triazine,
2-(2'-hydroxy-4'-[2-ethylhexyloxy])-4,6-bis(2-ethylhexyloxy)phenyl-1,3,5-triazine,
2-(2'-hydroxyphenyl)-4,6-bis(4-methoxyphenyl)-1,3,5-triazine,
2-(2',4'-dihydroxyphenyl)-4,6-bis(4-methoxyphenyl)-1,3,5-triazine,
2-(2'-hydroxy-3'-methylphenyl)-4,6-bis(4-methoxyphenyl)-1,3,5-triazine,
2-(2',3'-dihydroxyphenyl)-4,6-bis(4-methoxyphenyl)-1,3,5-triazine,
2-(2'-hydroxy-5'-chlorophenyl)-4,6-bis(4-methoxyphenyl)-1,3,5-triazine,
2-(2'-hydroxy-4-methoxyphenyl)-4,6-bis(4-methoxyphenyl)-1,3,5-triazine,
2-(2',4'-dihydroxyphenyl)-4,6-bis(4-methoxyphenyl)-1,3,5-triazine,
2-(2'-hydroxy-4-hexyloxyphenyl)-4,6-bis(4-methoxyphenyl)-1,3,5-triazine,
2-(2'-hydroxy-4-hexyloxyphenyl)-4,6-bis(3-methoxyphenyl)-1,3,5-triazine,
2-(2-hydroxy-4-methoxyphenyl)-4-(4-methoxyphenyl)-6-phenyl-1,3,5-triazine,
2-(2'-hydroxy-4'-[2-ethylhexyloxy])-4,6-bis(2-ethylhexyloxy)phenyl-1,3,5-triazine,
4,6-bis(2-hydroxy-4-methoxyphenyl)-2-(2-propoxyethoxy)-1,3,5-triazine,
4,6-bis(2-hydroxy-4-propoxyphenyl)-2-(2-methoxyethoxy)-1,3,5-triazine,
4,6-bis(2-hydroxy-4-ethoxyphenyl)-2-(2-methoxyethoxy)-1,3,5-triazine,
4,6-bis(2-hydroxy-4-methoxyphenyl)-2-(2-methoxyethoxy)-1,3,5-triazine,
4,6-bis(2-hydroxy-4-methoxyphenyl)-2-(2-ethoxyethoxy)-1,3,5-triazine,
4,6-bis(2-hydroxy-4-methoxyphenyl)-2-[2-(2-ethoxyethoxy)ethoxy]-1,3,5-triazine,
4,6-bis(2-hydroxy-4-ethoxyphenyl)-2-(2-ethoxyethoxy)-1,3,5-triazine,
4,6-bis(2-hydroxy-4-ethoxyphenyl)-2-[2-(2-ethoxyethoxy)ethoxy]-1,3,5-triazine,
4,6-bis(2-hydroxy-4-ethoxyphenyl)-2-(2-ethoxy-2-methylethoxy)-1,3,5-triazine,
4,6-bis(2-hydroxy-4-ethoxyphenyl)-2-(ethoxymethoxy)-1,3,5-triazine,
4,6-bis(2-hydroxy-4-methoxyphenyl)-2-octyloxy-1,3,5-triazine,
4,6-bis(2-hydroxy-4-methoxyphenyl)-2-{2-[2-(2-ethoxy)ethoxy]ethoxy}ethoxytriazine,
4,6-bis(2-hydroxy-4-ethoxyphenyl)-2-{2-[2-(2-ethoxy)ethoxy]ethoxy}ethoxy-1,3,5-triazine, and
4,5-bis(2-hydroxy-4-ethoxyphenyl)-2-butoxy-1,3,5-triazine.

(T=percentage transmission of a solution of 1 mg of substance in 100 ml of chloroform at a layer thickness of 1 cm; λ [m] is the maximum extinction coefficient).

The compounds of the formulae (3), (4) and (5) are known and can be prepared in a manner known per se, for instance by heating an amidine and an o-hydroxybenzenecarboxylic acid ester, preferably in the approximate molar quantitative ratio of 2:1 in boiling, organic solvents [cf. U.S. Pat. No. 3,896,125 and Helv. Chim. Acta 55, 1566–1595 (1972)].

Furthermore, structural elements of triazine UV absorbers of the formula

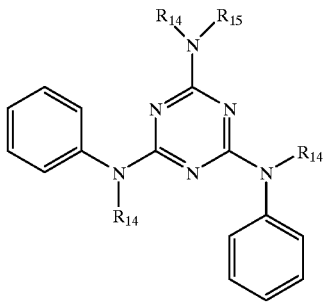

(6)

can be used as ($Q_2$).

$R_{14}$ and $R_{15}$ in this case are, independently of one another, hydrogen, hydroxyl, $C_1$–$C_5$alkyl or $C_1$–$C_5$alkoxy.

The benzotriazoles $Q_3$ are compounds of the formula

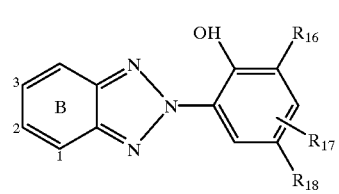

(7)

in which $R_{16}$ and $R_{18}$, independently of one another, are hydrogen, $C_1$–$C_{18}$alkyl or $C_1$–$C_8$alkoxy which is unsubstituted or substituted by phenyl, or halogen or the group

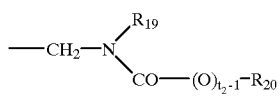  (7a)

in which $R_{19}$ is hydrogen, $C_1-C_{10}$alkyl, $C_5-C_8$cycloalkyl, $C_7-C_{10}$aralkyl or $C_6-C_{10}$aryl, $R_{20}$ is hydrogen, $C_1-C_{20}$alkyl, $C_2-C_{17}$alkenyl, $C_5-C_8$cycloalkyl, $C_7-C_{10}$aralkyl or $C_6-C_{10}$aryl, and $t_2$ is 1 or 2, and, if $t_2=1$, $R_{19}$ and $R_{20}$ together with the bridge member

can also form a mono- or polynuclear nitrogen-containing heterocycle and in this case $R_{19}$ is —CO— or methylene which is unsubstituted or substituted by $C_1-C_5$alkyl and $R_{20}$ is $C_2-C_5$alkylene, $C_2-C_5$alkenylene, $C_6-C_{10}$arylene or vicinally bonded di-, tetra- or hexahydro-$C_6-C_{10}$arylene, $R_{17}$ is $C_1-C_{18}$alkyl, $C_1-C_{18}$alkoxy, halogen, $C_6-C_{10}$aryl, $C_7-C_{10}$aralkyl or $C_5-C_8$cycloalkyl, and the ring B can be substituted in positions 1, 2 and 3 by $C_1-C_5$alkyl, $C_1-C_5$alkoxy, carboxyl, $C_2-C_9$alkoxycarbonyl, $H_2NCO—$, $SO_2—$, $C_1-C_5$alkylsulphonyl, halogen or by the radical of the formula

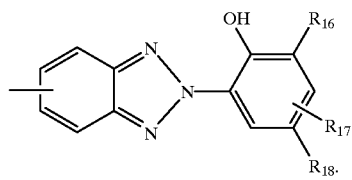  (7b)

The substituents $R_{19}$ and $R_{20}$ with the meaning of $C_1-C_{10}$alkyl and $C_1-C_{20}$alkyl can be straight-chain or branched hydrocarbon radicals, for example methyl, ethyl, n-propyl, isopropyl, n-butyl, isobutyl, sec-butyl, tert-butyl, pentyl, isopentyl, tert-pentyl, n-hexyl, 2-ethylhexyl, n-heptyl, n-octyl, isooctyl, n-nonyl, isononyl, n-decyl, n-dodecyl, heptadecyl, octadecyl or eicosyl.

If $R_{19}$ and $R_{20}$ are $C_6-C_{10}$aryl, then it can be a mono- or bicyclic aromatic radical, for example phenyl or naphthyl.

As $C_7-C_{10}$aralkyl, $R_{19}$ and $R_{20}$ are, for example, benzyl, phenethyl, α-methylphenethyl or α,α-dimethylbenzyl.

If $R_{19}$ and $R_{20}$ are $C_5-C_8$cycloalkyl, it can be cyclopentyl, cycloheptyl, cyclooctyl or preferably cyclohexyl.

$R_{20}$ as $C_2-C_{17}$alkenyl radicals are, for example, vinyl, allyl, 1-propenyl, 2-butenyl, 2-pentenyl, 2-hexenyl, 2-decenyl, 3,6,8-decatrienyl or 2-heptadecenyl.

Preferred benzotriazole compounds are those of the formula

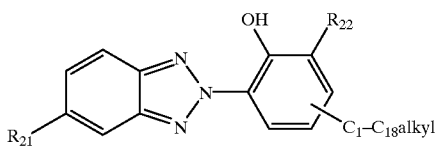  (8)

in which $R_{21}$ is $C_1-C_{18}$alkyl or preferably hydrogen, and $R_{22}$ is $C_1-C_{18}$alkyl which is unsubstituted or substituted by phenyl.

For the benzotriazole compounds of the formulae (7) and (8), the following may be mentioned by way of example:
2-(2'-hydroxy-5'-methylphenyl)benzotriazole,
2-(2'-hydroxy-5-tert-butylphenyl)benzotriazole,
2-(2'-hydroxy-3'-tert-butyl-5'-methylphenyl)-5-chlorobenzotriazole,
2-(2'-hydroxy-3'-5'-di-tert-butylphenyl)-5-chlorobenzotriazole,
2-(2'-hydroxy-5'-tert-octylphenyl)benzotriazole,
2-(2'-hydroxy-3'-acryloylamidomethyl-5'-methylphenyl)benzotriazole,
2-(2'-hydroxy-3'-acryloylamidomethyl-5'-benzylphenyl)benzotriazole,
2-(2'-hydroxy-3'-butoxacetamidomethyl-5'-benzylphenyl)benzotriazole,
2-(2'-hydroxy-3'5'-di-tert-amylphenyl)benzotriazole, and
2-(2'-hydroxy-3',5'-di-tert-butylphenyl)benzotriazole.

The benzotriazole compounds of the formulae (7) and (8) known to be UV-absorbing are for the most part described in FR-A-1 195 307 or U.S. Pat No. 3,629,192.

The benzophenones ($Q_4$) are compounds of the formula

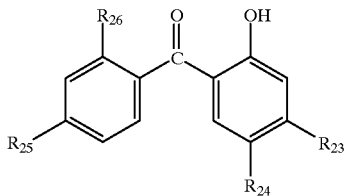  (9)

in which $R_{23}$ is hydrogen, hydroxyl, $C_1-C_{14}$alkoxy, phenoxy or amino, where $C_1-C_{14}$alkoxy can be substituted by a radical of the formula

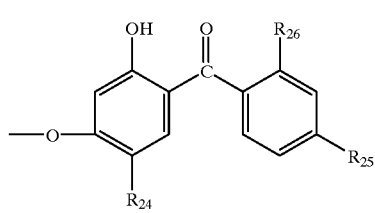  (9a)

and/or an acyloxy radical, $R_{24}$ is hydrogen, halogen or $C_1-C_5$alkyl, $R_{25}$ is hydrogen, hydroxyl or $C_1-C_5$alkoxy, and $R_{26}$ is hydrogen or hydroxyl.

Acyl is $C_1-C_5$alkanoyl, for example formyl, acetyl, propionyl, acryloyl, methacryloyl or benzoyl.

The compounds of the formula (9) can be prepared by processes known per se, such as are described, for example, in U.S. Pat. Nos. 3,468,938, 3,696,077 and U.S. Pat. No. 4,698,064.

The UV chromophores ($Q_5$) employed as para-aminobenzoic acid derivatives in liposomes according to the invention are compounds of the formula

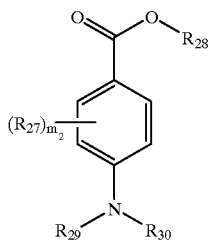
(10)

in which $R_{27}$ is hydroxyl, halogen, cyano, $C_1$–$C_5$alkyl, $C_1$–$C_5$alkoxy, mono-$C_1$–$C_5$alkylamino or di-$C_1$–$C_5$alkylamino, $R_{28}$ is hydrogen or $C_1$–$C_5$alkyl, $R_{29}$ and $R_{30}$, independently of one another, are hydrogen or $C_1$–$C_5$alkyl, and $m_2$ is 0, 1 or 2.

Preferably, as UV chromophores ($Q_5$), structural elements are employed which are derived from para-aminobenzoic acid or its methyl or ethyl ester.

Suitable UV chromophores ($Q_6$) are benzylidenecamphors. They are of the formula

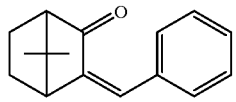
(11)

For the preparation of the liposomogenic UV absorbers according to the invention, the suitable UV chromophores ($Q_1$)–($Q_6$), if in this case they are poorly water-soluble compounds, are employed as aqueous dispersions.

Suitable dispersing agents in this case are various compounds, such as acid esters or their salts of alkylene oxide adducts, polystyrene sulphonates, fatty acid taurides, alkylated diphenylene oxide mono- or disulphonates, sulphonates of polycarboxylic acid esters, or the addition products of 1 to 60, preferably 2 to 30, mol of ethylene oxide and/or propylene oxide converted into an acidic ester with an organic dicarboxylic acid, or an inorganic polybasic acid, of fatty amines, fatty amides, fatty acids or fatty alcohols each having 8 to 22 carbon atoms or of tri- to hexahydric alkanols having 3 to 6 carbon atoms, lignosulphonates and formaldehyde condensation products. Details of the dispersing agents and the preparation of the UV absorber dispersions can be found, for example, in EP-A-0 523 006.

Preferably, the following chromophores Q are employed according to the invention:

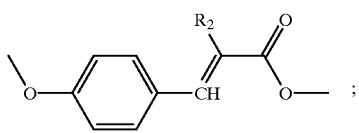
(2a)

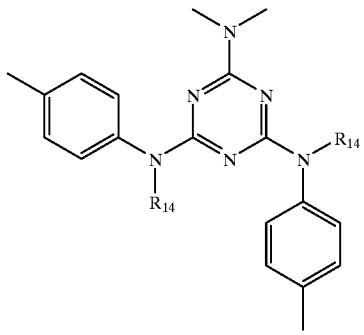
(6a)

or

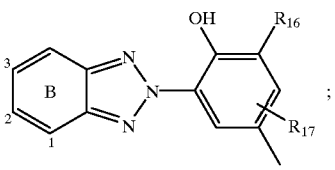
(7a)

$R_2$, $R_{14}$, $R_{16}$, $R_{17}$ and B are in each case defined as in the formulae (2), (6) and (7).

As a rule, the organic radical W is an at least divalent alkylene radical which can be interrupted, if desired, by a carbonyl, carboxylato or ether group. W, in particular, is a branched or preferably straight-chain alkylene group having 2 to 8 carbon atoms. The alkylene group preferably has 2 to 5 carbon atoms. It is, for example, the —$CH_2$—;—$CH_2CH_2$—;

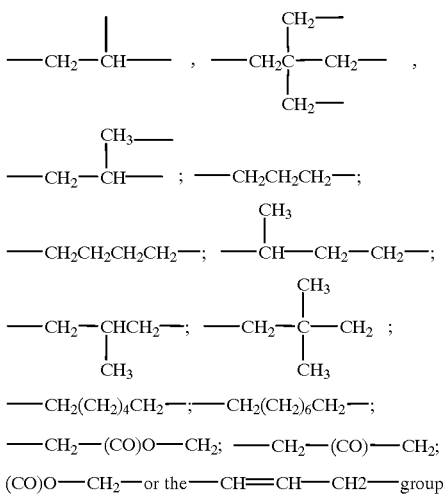

Suitable hydrophilic radicals $Z_1$ and $Z_2$ are preferably
($Z_a$) ammonium or amine compounds,
($Z_b$) phosphate compounds,
($Z_3$) carboxylate compounds, ($Z_d$) polyols, and ($Z_e$) sulphate compounds.

They form the hydrophilic head groups of the liposomogenic UV absorbers according to the invention. In these structural elements, a differentiation can be made between cationic ($Z_a$), anionic (($Z_b$), ($Z_c$), ($Z_e$)) and neutral head groups (($Z_a$) and ($Z_d$)).

Suitable cationic ammonium compounds ($Z_a$) are, in particular, mono- or di-$C_1$–$C_5$alkylammonium compounds, which can be modified by further substituents. The following groups may be mentioned by way of example:

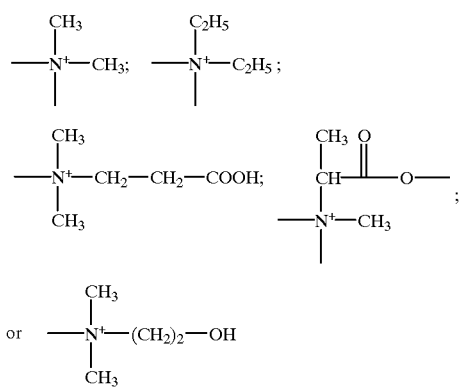

Suitable neutral amine compounds are, for example, the groups

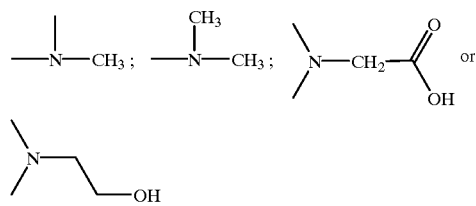

Suitable phosphate groups $Z_b$ are, in particular, compounds which are derived from mono- and diesters of phosphoric acid. The phosphorus compounds are in this case usually used in the form of their sodium salts.

The carboxylate compounds ($Z_c$) are derived from lower mono- or dicarboxylic acids and are likewise usually used as sodium salts.

Suitable polyols ($Z_e$) are, for example, the following compounds:

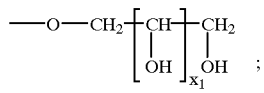

$X_1$ = 1,2,3 oder 4

(12a)

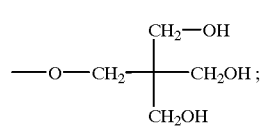

(12b)

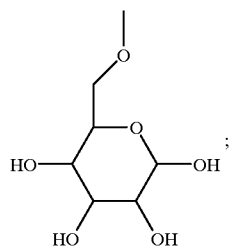

(12c)

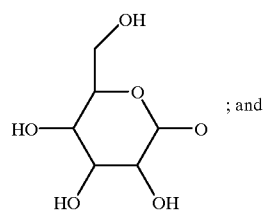

(12d)

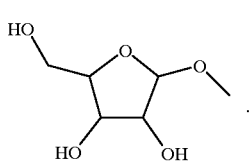

(12e)

The sulphate compounds ($Z_e$) are derived from alkyl sulphates which, it desired, can also be further substituted. Suitable sulphate groups are primarily the sulphate ion, $SO_4^{2-}$, Depending on which starting compounds are used, the head groups ($Z_a$)–($Z_e$) can simultaneously form the unit —W—$Z_1$ or —W—$Z_2$— with the organic radical W.

The liposomogenic UV absorbers according to the invention can be prepared by methods known per se. As a rule, they are prepared by a systematic sequence of reaction steps known per se, such as condensation, alkylation, esterification, hydrolysis etc. Details for carrying out the reactions can be taken from monographs for organic synthesis, such as J. March, Advanced Organic Chemistry, 2nd Edition, McGraw-Hill, New York, 1977.

The introduction of the hydrophobic radicals A can be carried out in very different ways, for example by etherification of the phenolic OH group of the UV chromophore (cf. Examples 1, 2, 5 and 7) or by reaction of an acid chloride with a long-chain dialkylamine (cf. Example 4). A multiplicity of reactions are likewise suitable for the introduction of the hydrophilic head groups Z, such as can be seen from Examples 1 and 2 (quaternization). With a suitable reaction procedure, A and Z, however, can also be introduced simultaneously, i.e. in one reaction step. This is achieved, for example, by opening a suitable acid anhydride using a fatty alcohol (Example 6).

Very particularly preferred liposomogenic compounds are those of the formula $$[(A_1)_{n_1}(Q)_p(W)_q]_{s_2}\text{—}(Z_1)_{r_1} \quad (13)$$

in which $A_1$ is a hydrophobic radical,

Q is a UV chromophore,

W is an organic radical, $Z_1$ is a hydrophilic radical, $n_1$ is a number from 1 to 4, p is 1 or 2, q is 1 to 3, $r_1$ is 1 or 2, and $s_2$ is 1 to 3.

Furthermore, preferred compounds are those of the formula

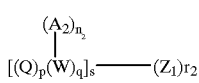

(14)

in which $A_2$ is a hydrophobic radical,

Q is a UV chromophore,

W is an organic radical, $Z_1$ is a hydrophilic radical, $n_2$ is 1 or 2, p is 1 or 2, q is 1 to 3, $r_2$ is 1 or 2, and s is 1 or 2.

Of the liposomogenic UV absorbers according to the invention which as a UV chromophore contain a structural element of a cinnamic acid derivative, the compounds of the formula

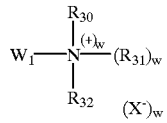

(15)

are preferred in which $W_1$ is a radical of the formula

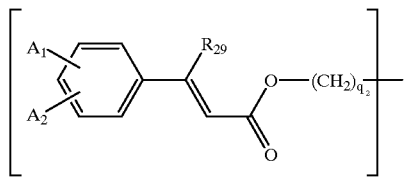

(15a)

$R_{29}$ is hydrogen, $C_1$–$C_4$alkyl or —CN, $R_{30}$ and $R_{31}$, independently of one another, are $C_1$–$C_5$alkyl, hydroxyl, hydroxy-$C_1$–$C_5$alkyl or carboxyl, $R_{32}$ is $C_1$–$C_5$alkyl, hydroxyl, hydroxy-$C_1$–$C_5$alkyl, carboxyl or a radical of the formula (15a), $A_1$ and $A_2$, independently of one another, are hydrogen or a $C_{10}$–$C_{14}$alkoxy radical, where one radical is always a $C_{10}$–$C_{14}$alkoxy radical, X is a halogen atom, q is a number from 2 to 4, and w is 0 or 1, or compounds of the formula

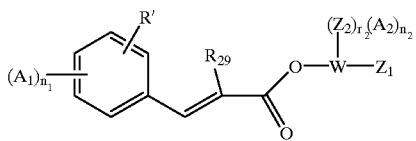

(16)

in which $R_{29}$ is hydrogen, $C_1$–$C_4$alkyl or —CN,

R' is hydrogen, $C_1$–$C_4$alkyl or $C_1$–$C_4$alkoxy, $A_1$ and $A_2$, independently of one another, are a $C_{10}$–$C_{14}$alkoxy radical, W is a $C_2$–$C_4$alkylene radical which, if desired, is interrupted by an —O(CO)— group, and $Z_1$ and $Z_2$, independently of one another, are the radical of a $C_1$–$C_3$carboxylic acid, $n_1$ and $n_2$, independently of one another, are 0, 1 or 2, $n_1$=$n_2$=0 not being additionally included, and $r_2$ is 1 or 2.

Preferred liposomogenic UV absorbers according to the invention, which have a triazine radical as a UV chromophore, are those of the formula

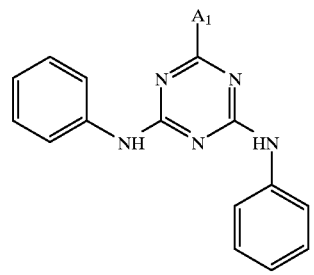

(17)

in which $A_1$ is a radical of the formula

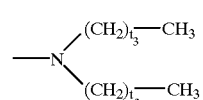

(17a)

(17b)

and $t_3$ and $t_4$, independently of one another, are a number from 5 to 13.

Preferred liposomogenic UV absorbers according to the invention, which have a benzylidenecamphor as a UV chromophore are those of the formula

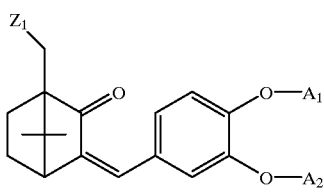

(18a)

or the formula

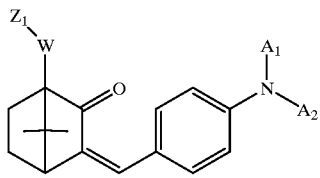

(18b)

in which $A_1$ and $A_2$, W and Z, are as defined in formula (1).

The liposomogenic UV absorbers according to the invention are preferably suitable as sunscreen agents in cosmetic preparations.

The invention therefore further relates to a cosmetic preparation, comprising at least one compound of the general formula (1) and cosmetically tolerable excipients or auxiliaries.

The cosmetic composition according to the invention contains 0.1 to 15, preferably 0.5 to 10% by weight, based on the total weight of the composition, of a liposomogenic UV absorber and a cosmetically tolerable auxiliary.

The cosmetic composition can be prepared by physical mixing of the liposomogenic UV absorber with the auxiliary by customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or non-ionic amphiphilic lipid, as a gel, solid stick or as an aerosol formulation.

As a water-in-oil or oil-in-water emulsion, the cosmetically tolerable auxiliary preferably contains 5 to 50% of an oil phase, 5 to 20% of an emulsifier and 30 to 90% of water.

The oil phase can in this case contain any oil suitable for cosmetic formulations, such as one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

Any emulsifier which can be employed conventionally can be used for the cosmetic formulations according to the invention, for example one or more ethoxylated esters of natural derivatives, such as polyethoxylated esters of hydrogenated castor oil, or a silicone oil emulsifier such as silicone polyol, a free or ethoxylated fatty acid soap, an ethoxylated fatty alcohol, a free or ethoxylated sorbitan ester, an ethoxylated fatty acid or an ethoxylated glyceride.

The cosmetic formulation can also contain further components such as emollients, emulsion stabilizers, skin moisture retainers, skin tanning accelerators, thickening agents such as xanthan, moisture retention agents such as glycerol, preservatives or fragrances and colorants.

The cosmetic formulations according to the invention are distinguished by excellent protection of the human skin against the harmful effect of sunlight with, at the same time, safer tanning of the skin. Moreover, the cosmetic preparations according to the invention are extremely wash-resistant when applied to the skin.

EXAMPLES OF PREPARATION OF THE NOVEL COMPOUNDS

Example 1

Bis{2-[3-(4-dodecyloxyphenyl)acryloyloxy]ethyl}dimethylammonium methylsulphate or iodide

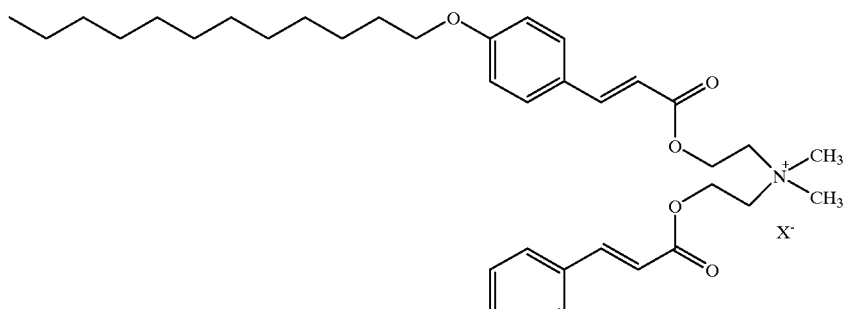

(101)

X=CH$_3$SO$_4$ (101a)

X=I (101b)

The preparation of 4-Dodecyloxycinnamic acid is carried out according to generally known processes by condensation of a 4-alkoxybenzaldehyde with malonic acid or by reaction of coumaric acid with dodecyl bromide. The colourless crystals have a melting point of 158–159 C. The corresponding acid chloride is obtained almost quantitatively therefrom by reaction with oxalyl chloride in benzene (18 hours, room temperature).

28.1 g (0.08 mol) of 4-dodecyloxycinnamoyl chloride are initially introduced in 150 ml of chloroform and, with stirring and cooling at room temperature, treated first with 4.1 g (0.04 mol) of triethylamine, then with 5.0 g (0.04 mol)

of N-methyldiethanolamine. The mixture is additionally stirred for about 4 hours and cooled to 10 C., and the reaction solution is added dropwise to 250 ml of chloroform, which has previously been saturated with $NH_3$, to liberate the base. The suspension is filtered twice through Hyflo® and evaporated to dryness. The crude amine can be purified by column chromatography (silica gel, toluene/ethanol 95:5). The yield is 53% of theory.

For quaternization, the amine is initially introduced in toluene and reacted at 40 C. with the molar amount of dimethyl sulphate (=101a) or methyl iodide (=101b). After 3 hours, the thin-layer chromatogram is free of starting material. The mixture is evaporated to dryness in vacuo and treated with acetone to crystallize it. The colourless crystals are washed with acetone, then with hexane, and dried at 40 C. The quaternization proceeds almost quantitatively.

UV spectrum ($10^{-5}$ M; ethanol): $\lambda_{max}$=313 nm $\epsilon_{max}$=53,500 $M^{-1}$ $cm^{-1}$

Example 2

{2-[3-(3,4-Bis-dodecyloxyphenyl)acryloyloxy] ethyl}-(2-hydroxyethyl)dimethylammonium bromide

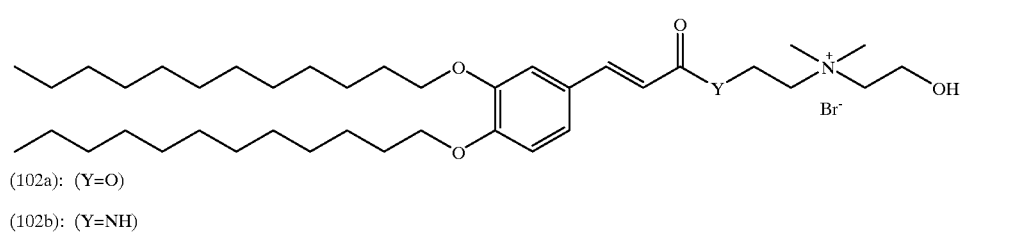

(102a): (Y=O)

(102b): (Y=NH)

The preparation of 3,4-bis-dodecyloxycinnamic acid and the corresponding acid chloride is carried out in analogy to the process described in Example 1. To esterify and liberate the amine base, reaction with 2-dimethylaminoethanol is likewise carried out analogously to Example 1.

The quaternization with 2-bromoethanol is carried out in toluene at 100 C. in the course of 12 hours. The crude product can be further purified by washing with acetone and subsequent column chromatography.

UV spectrum ($10^{-5}$ M; ethanol): $\lambda$=328 nm $\epsilon_{max}$=19,500 $M^{-1}cm^{-1}$

Example 3

{2-[3-(3,4-Bis-dodecyloxyphenyl)acryloylamino] ethyl}-(2-hydroxyethyl)dimethylammonium bromide The synthesis of this compound is carried out following the process described in Example 2. Instead of the esterification, reaction is carried out with 2-dimethylaminoethylamine to give the amide. The product can be purified by triturating with acetone and recrystallizing from methanol.

UV spectrum ($10^{-5}$ M; ethanol): $\lambda_{max}$=321 nm $\epsilon_{max}$=19,500 $M^{-1}cm^{-1}$

Example 4

2,4-Bis[(4-carboxyl)anilino]-6-dioctadecylamino-s-triazine (sodium salt)

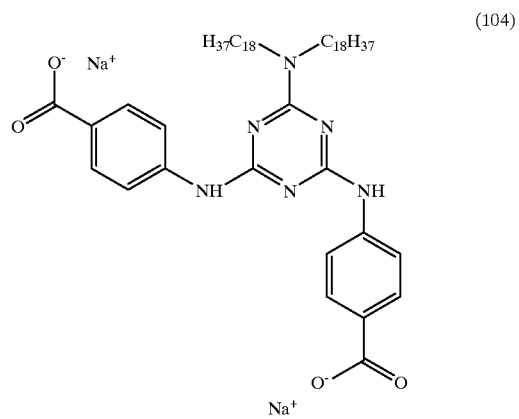

18.5 g (0.1 mol) of cyanuric chloride are initially introduced at 0–5 C. in 250 ml of a dioxane/water (9:1) mixture.

16.5 g (0.1 mol) of ethyl 4-aminobenzoate is introduced with stirring and the temperature is allowed to climb to 15 C., the pH falling to 0.5. The white suspension is adjusted to a pH of 8.0–8.5 using 30% NaOH and treated with a further equivalent of amine. It is diluted with 250 ml of dioxane/water and heated to 90 C., the pH being kept at 8.5 by automatic metering-in of NaOH. After 4 hours, the solid is filtered off with suction and washed with dioxane, water and methanol. The crude intermediate is purified by recrystallization from ethylcellosolve (yield: 25.7 g; 58% of theory; melting point 264 C.).

6.63 g (0.015 mol) of the intermediate and 1.83 g (0.015 mol) of 4-dimethylaminopyridine are initially introduced in 70 ml of DMF and treated at 60 C. with 8.3 g of dioctadecylamine, dissolved in 30 ml of chloroform. The mixture is stirred at 100 C. for 3 hours, and the hot solution is filtered and evaporated to dryness. The residue is extracted with 50 ml of toluene/ethyl acetate (80:20) and purified by column chromatography (silica gel) (yield: 4.5 g; 33% of theory; colourless, waxy ester).

For hydrolysis, the ethyl ester is initially introduced in an ethanol/NaOH mixture and heated at reflux for 2 hours. The gelatinous precipitate is filtered off and washed with acetone. Hydrolysis takes place almost quantitatively.

UV spectrum ($10^{-5}$ M; ethanol): $\lambda_{max}$=301 nm $\epsilon_{max}$=60,000 $M^{-1}cm^{-1}$

Example 5

Mono{3-[3-(3,4-bis-dodecyloxyphenyl)acryloyloxy]-2-hydroxypropyl}2,3-diacetoxysuccinate

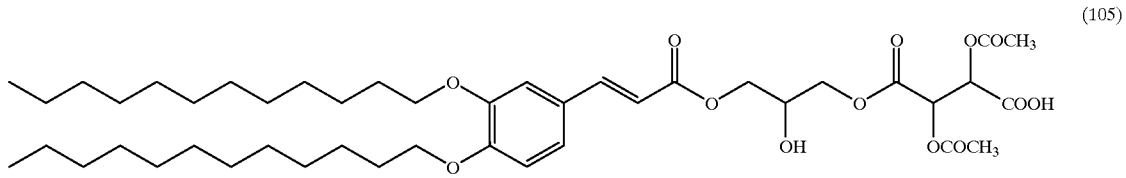

(105)

The preparation of 3,4-bis-dodecyloxycinnamic acid and of the corresponding acid chloride is carried out analogously to the process described in Example 1. The monoglyceride is obtained therefrom in almost quantitative yield following a procedure of Watanabe et al. (J. Med. Chem. 1980, 23, 50–59) by esterification with isopropylideneglycerol and subsequent removal of the protective group with boric acid.

A mixture of 5.91 g (0.01 mol) of monoglyceride and 2.16 g (0.01 mol) of diacetyltartaric anhydride is heated at 120 C. for 2 hours under protective gas. The glassy crude product can be purified by column chromatography (silica gel; toluene/acetone 8:2).

UV spectrum ($10^{-5}$ M; ethanol): $\lambda_{max}$=328 nm $\epsilon_{max}$=17,400 $M^{-1}cm^{-1}$ The preparation of 4-dodecyloxycinnamoyl chloride is carried out as described in Example 1.

30.9 g (0.088 mol) of acid chloride are initially introduced together with 5.36 g (0.04 mol) of DL-malic acid and 100 ml of chlorobenzene and heated to 130 C. under inert gas. After stirring for 2 hours, evolution of HCl is complete. 7.7 g (0.04 mol) of 1-dodecanol, dissolved in 10 ml of chlorobenzene, are then added dropwise and the mixture is stirred at reflux for a further 3 hours. After cooling, the precipitate is filtered off with suction, washed with toluene and hexane and dried at 80 C. in vacuo. The crude product can be purified by column chromatography (silica gel, toluene/acetone 80:20). The yield is 15.2 g (62% of theory).

UV spectrum ($10^{-5}$ M; ethanol): $\lambda_{max}$=311 nm $\epsilon_{max}$=27,300 $M^{-1}cm^{-1}$

Example 6

1-Dodecyl 2-[3-(4-dodecyloxyphenyl)acryloyloxy]succinate

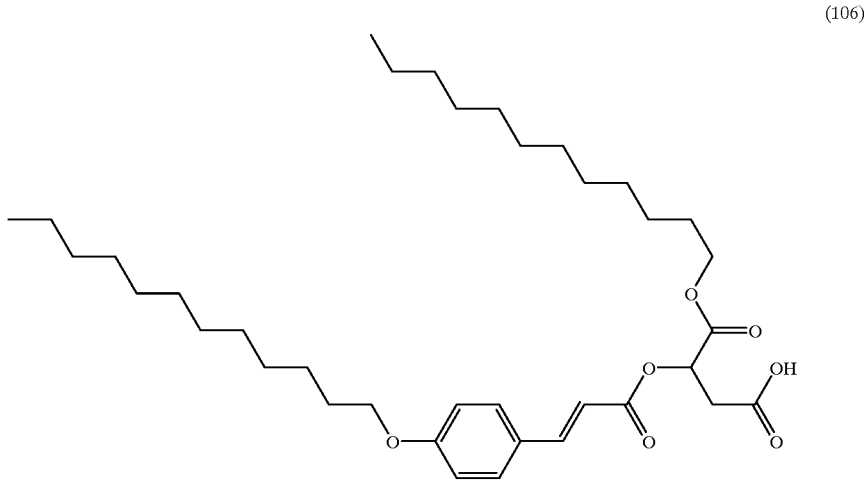

(106)

Example 7

Bis{2-[3-(4-dodecyloxyphenyl)acryloyloxy]ethyl}aminoacetic acid

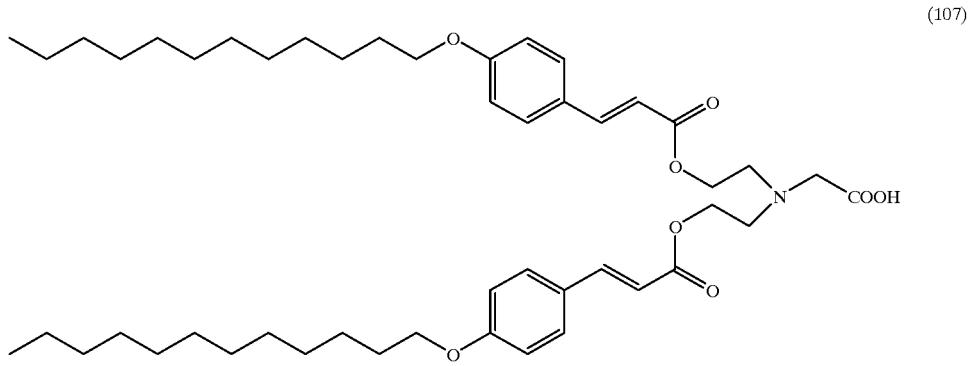

(107)

26.7 g (0.075 mol) of 4-dodecyloxycinnamoyl chloride (preparation see Example 1) and 4.9 g (0.03 mol) of N,N-bis(hydroxyethyl)glycine are well mixed and slowly heated to 130–140 C. under inert gas. Above 80 C., the batch becomes stirrable and evolution of HCl occurs. After 4 hours, the reaction is complete. After cooling, 100 ml of acetone/water (95:5) are added and the mixture is heated under reflux for 2 hours. It is evaporated to dryness and purified by column chromatography (silica gel, toluene/acetone 80:20). The yield of the strongly hygroscopic product is 3.1 g (13% of theory).

UV spectrum ($10^{-5}$ M; ethanol): $\lambda_{max}$=313 nm $\epsilon_{max}$=29,300 $M^{-1}cm^{-1}$

Example 8

1-{2-[3-(4-Methoxyphenyl)acryloyloxy]ethyl}2-dodec-2-enylsuccinate (triethanolamine salt)

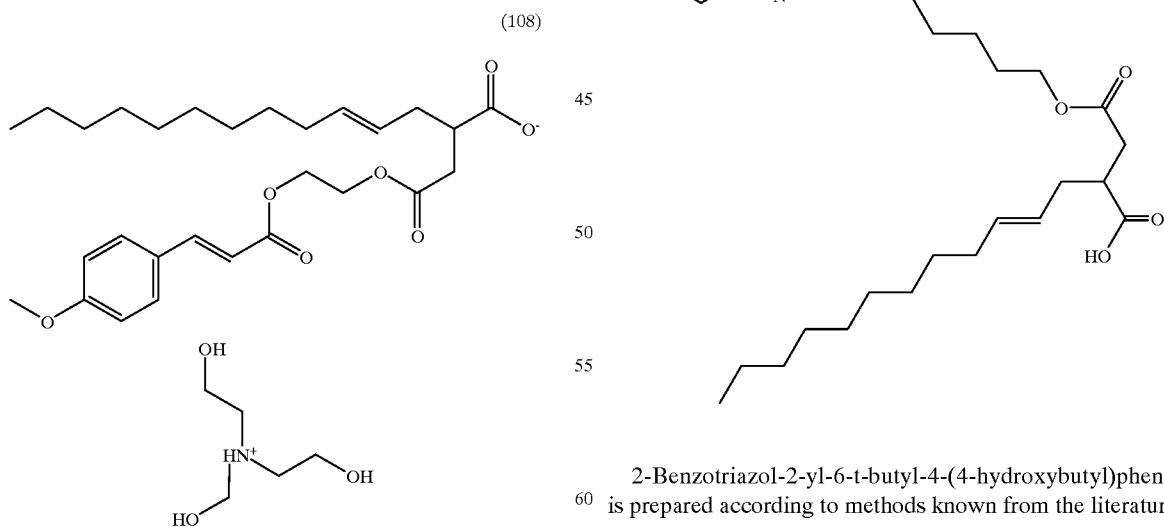

(108)

2-Hydroxyethyl 4-methoxycinnamate is prepared by methods known from the literature (esterification).

9.0 g (0.04 mol) of 2-hydroxyethyl 4-methoxycinnamate and 10.6 g (0.04 mol) of 2-dodecenylsuccinic anhydride are dissolved in 50 ml of toluene and stirred at 100–110 C. After 6 hours, the thin-layer chromatogram shows almost quantitative conversion. The mixture is cooled to 55–60 C. and treated with 5.35 g (0.036 mol) of triethanolamine. It is additionally stirred for 6 hours and the solvent is removed in vacuo. 24.9 g (97.7% of theory) of the lightly coloured, highly viscous product are obtained.

UV spectrum ($10^{-5}$ M; ethanol): $\lambda_{max}$=312 nm $\epsilon_{max}$=26,400 $M^{-1}cm^{-1}$

Example 9

1-{[1-Hydroxy-2-(2-benzotriazolyl)-6-t-butyl-4-(4-hydroxybutyl)]phenyl}2-dodec-2-enylsuccinate

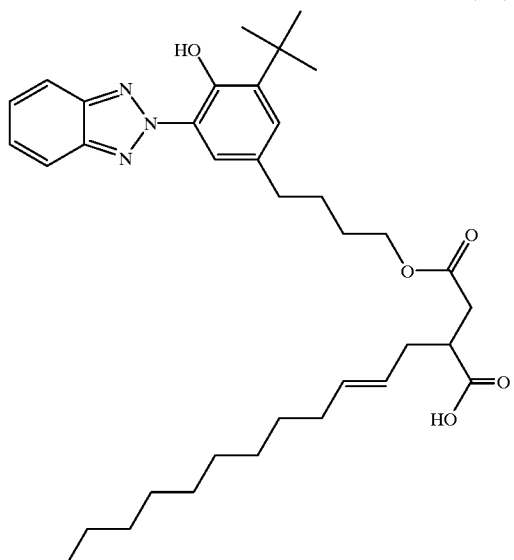

(109)

2-Benzotriazol-2-yl-6-t-butyl-4-(4-hydroxybutyl)phenol is prepared according to methods known from the literature.

8.5 g (0.025 mol) of 2-benzotriazol-2-yl-6-t-butyl-4-(4-hydroxybutyl)phenol and 6.9 g (0.025 mol) of 2-dodecenylsuccinic anhydride are dissolved in 100 ml of toluene and stirred under nitrogen at 100–110 C. After 18 hours, the thin-layer chromatogram shows almost quantitative conversion. The solvent is removed in vacuo and the residue is purified by column chromatography (toluene/ethyl acetate=9:1; silica gel 40×5 cm). 5.4 g of a lightly coloured, highly viscous product are obtained (36% of theory)

UV spectrum ($10^{-5}$ M; ethanol): $\lambda_{max}$=340 nm $\epsilon_{max}$=14,500 $M^{-1}cm^{-1}$

USE EXAMPLES

Example 10 a. Preparation of Liposomes

1–5 g of the compound of the formula (101a) (preparation cf. Example 1) are dissolved in 100 ml of N-methylpyrrolidone (NMP). This solution is then added dropwise to 900 ml of 0.9% aqueous NaCl solution or injected using a syringe, liposomes being formed. The volume of the resulting liposome suspension is concentrated to 50–100 ml with the aid of a diafiltration apparatus (Ultrasette, Skan AG, Basle) so that the liposomes are correspondingly concentrated to 1–10%. The solvent is then likewise exchanged with the aid of the diafiltration apparatus by further filtering and replacing the volume of the removed filtrate simultaneously by pure 0.9% NaCl solution. For solvent exchange, based on the concentrated liposome suspension, at least five times the volume of pure 0.9% NaCl solution is used. With an initial NMP content of 10%, at most 0.07% of NMP then still remains in the suspension. The residual content of NMP can be reduced as desired by increasing the volume of the 0.9% NaCl solution used for the exchange.

Alternatively, liposomes are prepared by first dissolving 1–5 g of the compound of the formula (101a) again in 100 ml of solvent (NMP, ethanol or diethyl ether). The solution is then added to a round-bottomed flask and heated, and the solvent is stripped off in vacuo using a rotary evaporator. 50–100 ml of 0.9% NaCl solution are then added to the resulting film on the inner wall of the flask and it is then shaken. The liposomes formed in this way are then sonicated for 10–60 minutes with the aid of an ultrasonic rod (Branson Model 250 Sonifier, Skan AG, Basle), which leads to the reduction in size of the liposomes.

b. Determination of the Diameter of the Liposomes

The diameter of the liposomes is determined with the aid of photon correlation spectroscopy (ALV/Monomode Fibre Compact Goniometer System, ALV-Laser GmbH, Langen). To do this, the liposome suspension is diluted to 0.02% to 0.1% and the autocorrelation function of the scattered light fluctuations is measured at four scattering angles (30, 60, 90 and 120). With the aid of the CONTIN software, mean diffusion coefficients are obtained therefrom which, in the case of angular dependence, are extrapolated to the scattering angle 0. The diameter of the liposomes follows from the resulting diffusion coefficient using the Stokes-Einstein relationship. For the liposomes of the compound of the formula (101a) prepared using the injection method, it is found that: d=(220 40) nm.

This counts as proof that liposomes are present. In the second method for liposome preparation, which is described under a, the diameter can be adjusted between 1000 and 200 nm by variation of the sonication time (10 to 60 minutes).

c. Testing of the Substantivity and Water Resistance

To test the substantivity and water resistance, stratum corneum from pigs' ears is used as an in vitro model. The pigs' ears are fetched from the slaughterhouse on the day of stratum corneum preparation. After the ears have been washed and the bristles shaved off, they are cut into pieces of size 3×3 cm. Immediately before peeling off the stratum corneum, the cut pieces are placed in double-distilled water at 60 C. for 1.5 minutes. The stratum corneum is then peeled off and stored in a penicillin/streptomycin solution (1% in double-distilled water) until use.

The substantivity and water resistance are then tested with the aid of Franz's diffusion cells. The UV absorber solution is first added to the lower compartment of a cell and 0.9% NaCl solution (adjusted to pH 7.4 with phosphate buffer) to the upper compartment. A piece of stratum corneum is placed between the two compartments with the outer side downwards such that the UV absorber molecules can diffuse into the skin or adsorb on the skin. During the course of this, the diffusion cell is temperature-controlled at 32 C. and the UV absorber solution in the cell is stirred. The adsorption kinetics are monitored for 5 hours by analysing the stratum corneum by UV spectroscopy after 60 minutes in each case. The crucial parameter for the assessment of the substantivity is the concentration of the UV absorber molecules in the skin which has been established after 5 hours. The UV absorber solution is then removed from the lower cell compartment and replaced by 0.9% NaCl solution (adjusted to pH 6.0 with phosphate buffer). The desorption kinetics are then measured for a further 17 hours in the same manner (however at greater time intervals), essential parameters for the assessment of water resistance being on the one hand the concentration of UV absorber molecules which still remains in the skin after 17 hours and on the other hand the ratio of this value, based on the maximum concentration immediately before the start of the desorption process.

The results listed in Table 1 show that after adsorption for 5 hours the concentration of the compound of the formula (101a) in the skin is very high.

TABLE 1

|  | Compound of the formula (101), 10 mM in liposomal form without further additives |
|---|---|
| c(skin, ads.), after 5 hours adsorption (substantivity) | (1.9 0.6) mM |
| c(skin, des.) after 17 hours desorption (water resistance) | (1.5 0.5) mM |
| $c(skin_{des})/c(skin_{ads})$ | 0.79 |

From the results in Table 1, it can furthermore be seen that the compound of the formula (101a) also has a very high water resistance. Thus after treatment for 17 hours with an aqueous solution (0.9% NaCl, adjusted to pH 6.0 with phosphate buffer), 79% of the substance still remains in the skin.

d. Spectral Properties

The maximum extinction of the compound of the formula (101a) lies at a wavelength of 310 nm. At this wavelength, the extinction of a 1% solution at an optical layer thickness of 1 cm is:

E (1%, 1 cm)=612.

The half-width of the absorption band is 58 nm.

e. Determination of Sun Protection Factors

Sun protection factors (SPF) are determined by the method of Diffey and Robson (J. Soc. Cosmet. Chem. 40 (1989)127). 2 of the formulation per $cm^2$ are thus applied to Transpore® tape (3M). The diffuse transmission (measurement using integration sphere) is then measured in the spectral range between 290 and 400 nm against uncoated Transpore® tape and, for the calculation of the sun protection factor, weighted using the sensitivity spectrum of the skin and the intensity spectrum of the sun. Nine measurements are carried out in each case, the highest and the lowest value of the resulting sun protection factors not being taken into account, so that the averaging is finally carried out using seven measurements. Thus for a 5% liposome suspension of the compound of the formula (101a):
SPF=8.6 1.7.

Example 11 a. Preparation of Liposomes

The liposomes are prepared as described in Example 10a, but instead of the compound of the formula (101a) the compound of the formula (101b) is used and instead of NMP as a solvent for the injection ethanol heated to 65 C. is used.

b. Determination of the Diameter of the Liposomes

The diameter of the liposomes is determined as described in Example 9b. For liposomes of the compound of the formula (101b) a value of:
d=(190 30) nm is obtained.

c. Testing of the Substantivity and Water Resistance

The substantivity and the water resistance are tested in a similar manner to that described in Example 9c. Table 2 shows the results of liposomes of the compound of the formula (101b). The same result is seen here as described in Example 9c for the compound of the formula (101a), namely excellent behaviour of the liposomogenic substance with respect to substantivity and water resistance.

d. Spectral Properties

The maximum extinction of the compound of the formula (101b) lies at a wavelength of 310 nm. At this wavelength the extinction of a 1% solution at an optical layer thickness of 1 cm is:

E (1%, 1 cm)=601.

The half-width of the absorption band is 58 nm.

e. Determination of Sun Protection Factors

The sun protection factor is determined in a similar manner to that described in Example 10b for the compound of the formula (101a). With a 5% suspension of the compound of the formula (101b) a value of SPF=8.3 1.6 results.

Example 12 a. Preparation of Liposomes

The liposomes are prepared in a similar manner to that described in Example 10a with the difference that instead of the compound of the formula (101a) the compound of the formula (102a) is used (preparation of the compound cf. Example 2). The solvent used for the injection is ethanol or NMP.

b. Determination of the Diameter of the Liposomes

The diameter of the liposomes is determined as described in Example 10b. For liposomes of the compound of the formula (102a) a value of:

d=(250 40) nm is obtained.

c. Testing of the Substantivity and Water Resistance

The substantivity and the water resistance are tested in a similar manner to that described in Example 9c. Table 3 shows the results of liposomes of the compound of the formula (102a).

TABLE 2

| | Compound of the formula (101b), 10 mM in liposomal form without further additives |
|---|---|
| c(skin, ads.), after 5 hours adsorption (substantivity) | (2.1 0.7) mM |
| c(skin, des.) after 17 hours desorption (water resistance) | (1.5 0.5) mM |
| c($skin_{des}$)/c($skin_{ads}$) | 0.71 |

TABLE 3

| | Compound of the formula (102a) |
|---|---|
| | 10 mM in liposomal form without further additives |
| c(skin, ads.), after 5 hours adsorption (substantivity) | (3.1 1.0) mM |
| c(skin, des.) after 17 hours desorption (water resistance) | (1.4 0.5) mM |
| c($skin_{des}$)/c($skin_{ads}$) | 0.45 |

Here too, the excellent behaviour of the liposomogenic substance according to the invention is seen with respect to substantivity and water resistance.

d. Spectral Properties

The maximum extinction of the compound of the formula (102a) lies at a wavelength of 328 nm. At this wavelength the extinction of a 1% solution at an optical layer thickness of 1 cm is:

E (1%, 1 cm)=273.

The half-width of the absorption band is 71 nm.

e. Determination of Sun Protection Factors

The sun protection factor is determined in a similar manner to that described in Example 9d. With a 5% suspension of the compound of the formula (102a) a value of SPF=3.0 0.3 results.

Example 13 a. Preparation of Liposomes

The liposomes are prepared as described in Example 10a with the difference that instead of the compound of the formula (101a) the compound of the formula (102b) is used. The solvent used for the injection is ethanol or NMP.

b. Determination of the Diameter of the Liposomes

The diameter of the liposomes is determined as described in Example 10b. For liposomes of the formula (102b) a value of:

d=(150 25) nm results.

c. Testing of the Substantivity and Water Resistance

The substantivity and the water resistance are tested as described in Example 9c. Table 4 shows the results of liposomes of the formula (102b).

TABLE 4

| | Compound of the formula (102b), |
|---|---|
| | 10 mM in liposomal form without further additives |
| c(skin, ads.), after 5 hours adsorption (substantivity) | (1.4 0.5) mM |
| c(skin, des.) after 17 hours desorption (water resistance) | (0.9 0.3) mM |
| c($skin_{des}$)/c($skin_{ads}$) | 0.64 |

A similar result to that in Example 10c is seen.

d. Spectral Properties

The maximum extinction of the compound of the formula (102b) lies at a wavelength of 328 nm. At this wavelength the extinction of a 1% solution at an optical layer thickness of 1 cm is:

E (1%, 1 cm)=274.

The half-width of the absorption band is 69 nm.

e. Determination of Sun Protection Factors

The sun protection factor was determined in a similar manner to that described in Example 10d. With a 5% suspension of the compound of the formula (102b) a value of SPF=3.0 0.3 results.

Example 14 a. Preparation of Liposomes

The liposomes are prepared as described in Example 10a, with the difference that instead of the compound of the formula (101a) the compound of the formula (104) is used (preparation of the compound cf. Example 4). The solvent used for the injection is ethanol or NMP.

b. Determination of the Diameter of the Liposomes

The diameter of the liposomes is determined as described in Example 10b. For liposomes of the compound of the formula (104) a value of:

d=(120 15) nm results.

c. Spectral Properties

The maximum extinction of the compound of the formula (104) lies at a wavelength of 303 nm. At this wavelength the extinction of a 1% solution at an optical layer thickness of 1 cm is:

E (1%, 1 cm)=654.

The half-width of the absorption band is 39 nm.

d. Determination of Sun Protection Factors

The sun protection factor is determined as described in Example 10b. With a 5% suspension of the compound of the formula (104) a value of SPF=5.0 0.5 results.

Example 15 a. Preparation of Liposomes

The liposomes are prepared as described in Example 10a, with the difference that instead of the compound of the formula (101a) the compound of the formula (105) is used (preparation of the compound cf. Example 5). The solvent used for the injection is ethanol or NMP.

b. Determination of the Diameter of the Liposomes

The diameter of the liposomes is determined as described in Example 10b. For liposomes of the formula (105) a value of:

d=(150 25) nm results.

c. Spectral Properties

The maximum extinction of the compound of the formula (105) lies at a wavelength of 328 nm. At this wavelength the extinction of a 1% solution at an optical layer thickness of 1 cm is:

E (1%, 1 cm)=215.

The half-width of the absorption band is 68 nm.

d. Determination of Sun Protection Factors

The sun protection factor is determined as described in Example 9d. With a 5% suspension of the compound of the formula (105) a value of SPF=2.3 0.3 results.

Example 16 a. Preparation of Liposomes

The liposomes are prepared as described in Example 9a, with the difference that instead of the compound of the formula (101a) the compound of the formula (106) is used (preparation of the compound cf. Example 6). The solvent used for the injection is ethanol or NMP.

b. Determination of the Diameter of the Liposomes

The diameter of the liposomes is determined as described in Example 10b. For liposomes of the formula (106) a value of:

d=(180 30) nm results.

c. Testing of the Substantivity and Water Resistance

The substantivity and the water resistance are tested as described in Example 10c. Table 5 shows the results of liposomes of the formula (106).

TABLE 5

| | Compound of the formula (106), 10 mM in liposomal form without further additives |
|---|---|
| $c(skin, ads.)$, after 5 hours adsorption (substantivity) | (5.5 0.9) mM |
| $c(skin, des.)$ after 17 hours desorption (water resistance) | (2.4 0.6) mM |
| $c(skin_{des})/c(skin_{ads})$ | 0.44 |

Here too, the excellent behaviour of the liposomogenic substance according to the invention is seen with respect to substantivity and water resistance.

d. Spectral Properties

The maximum extinction of the compound of the formula (106) lies at a wavelength of 312 nm. At this wavelength the extinction of a 1% solution at an optical layer thickness of 1 cm is: ps E (1%, 1 cm)=451.

The half-width of the absorption band is 50 nm.

d. Determination of Sun Protection Factors

The sun protection factor is determined as described in Example 9d. With a 5% suspension of the compound of the formula (106) a value of SPF=5.6 0.7 results.

Example 17 a. Preparation of Liposomes

The liposomes are prepared as described in Example 10a, with the difference that instead of the compound of the formula (101a) the compound of the formula (107) is used (preparation of the compound cf. Example 7). The solvent used for the injection is ethanol or NMP.

b. Determination of the Diameter of the Liposomes

The diameter of the liposomes is determined as described in Example 10b. For liposomes of the formula (107) a value of:

d=(980 130) nm results.

c. Spectral Properties

The maximum extinction of the compound of the formula (107) lies at a wavelength of 313 nm. At this wavelength the extinction of a 1% solution at an optical layer thickness of 1 cm is:

E (1%, 1 cm)=347.

The half-width of the absorption band is 52 nm.

d. Determination of Sun Protection Factors

The sun protection factor is determined as described in Example 10d. With a 5% suspension of the compound of the formula (107) a value of SPF=3.8 0.4 results.

Example 18 a. Preparation of Liposomes

The liposomes are prepared as described in Example 10a, with the difference that instead of the compound of the formula (101a) the compound of the formula (108) is used (preparation of the compound cf. Example 8). The solvent used for the injection is ethanol or NMP.

b. Determination of the Diameter of the Liposomes

The diameter of the liposomes is determined as described in Example 1b. For liposomes of the compound of the formula (108) a value of:

d=(170 30) nm results.

c. Spectral Properties

The maximum extinction of the compound of the formula (108) lies at a wavelength of 310 nm. At this wavelength the extinction of a 1% solution at an optical layer thickness of 1 cm is:

E (1%, 1 cm)=418.

The half-width of the absorption band is 53 nm.

d. Determination of Sun Protection Factors

The sun protection factor is determined as described in Example 10d. With a 5% suspension of the compound of the formula (108) a value of SPF=4.8 0.5 results.

Example 19 a. Preparation of Liposomes

The liposomes are prepared as described in Example 10a, with the difference that instead of the compound of the formula (101a) the compound of the formula (109) is used (preparation of the compound cf. Example 9). The solvent used for the injection is NMP.

b. Spectral Properties

The maximum extinction of the compound of the formula (109) lies at a wavelength of 339 nm. At this wavelength the extinction of a 1% solution at an optical layer thickness of 1 cm is:

E (1%, 1 cm)=237.

c. Determination of Sun Protection Factors

The sun protection factor is determined as described in Example 10d. With a 5% suspension of the compound of the formula (108) a value of SPF=5.5 results.

What is claimed is:

1. A liposomogenic UV absorber comprising a hydrophilic head group (=Z), a spacer (=W), a UV chromophore (Q) having an absorption in the range from 285 to 400 nm and at least one hydrophobic tail group (=A), which is of the formula $$[(A_1)_{n_1} - (Q)_p - W_q \begin{matrix} (Z_2)_{r_2} - (A_2)_{n_2} \\ \\ (Z_1)_{r_1} \end{matrix}]_s \quad (1)$$

in which
- $A_1$ and $A_2$, independently of one another, are a hydrophobic alkyl, alkoxy, acyl or alkylamino radical, the chains having at least 8 carbon atoms,
- Q is a UV chromophore selected from the group consisting of
  - ($Q_2$) triazine derivatives,
  - ($Q_3$) benzotriazoles,
  - ($Q_4$) benzophenones, and
  - ($Q_5$) p-aminobenzoic acid derivatives,
- W is a divalent alkylene radical,
- $Z_1$ and $Z_2$, independently of one another, are a hydrophilic radical selected from the class of ($Z_a$) ammonium or amine compounds, ($Z_b$) phosphate compounds, ($Z_3$) carboxylate compounds, ($Z_d$) polyols, and ($Z_e$) sulphate compounds,
- $n_1$ and $n_2$, independently of one another, are a number from 0 to 4, $n_1=n_2=0$ not being additionally included,
- p is 1 or 2,
- q is a number from 0 to 3,
- $r_1$ is 1 or 2,
- $r_2$ is 0 or 1, and
- s is a number from 1 to 3.

2. A liposomogenic UV absorber according to claim 1, wherein $A_1$ and $A_2$, independently of one another, are an alkyl or alkenyl radical having 10 to 14 carbon atoms.

3. A liposomogenic UV absorber according to claim 1, wherein $n_1$ and $n_2$ are 1 or 2.

4. A liposomogenic UV absorber according to claim 3, wherein $n_1$ and $n_2$ are 2.

5. A liposomogenic UV absorber according to claim 1, wherein the radicals $A_1$ and $A_2$ have the same meaning.

6. A liposomogenic UV absorber according to claim 1, wherein the UV chromophore ($Q_2$) is derived from an α-hydroxyphenyl-s-triazine compound of the formula (3)

in which
- $R_3$ and $R_4$, independently of one another, are $C_1$–$C_5$alkyl, $C_1$–$C_{18}$alkyl substituted by hydroxyl, $C_1$–$C_5$alkoxy, $C_1$–$C_5$alkylthio, amino or $C_1$–$C_5$mono- or dialkylamino, unsubstituted phenyl or phenyl substituted by chlorine, hydroxyl, $C_1$–$C_{18}$alkyl and/or $C_1$–$C_{18}$alkoxy;
- $R_5$ is $C_1$–$C_{18}$alkyl, $C_1$–$C_{18}$alkoxy, halogen, hydroxyl, a radical of the formula $$-(O-CH_2-CH_2-)_t-R_6; \quad (3a)$$

oder einen Rest der Formel (3b)

$$-O-V_1-\overset{O}{\underset{\|}{C}}-O-R_7$$

- $R_7$ is $C_1$–$C_5$alkyl or $C_1$–$C_5$alkoxy-$C_1$–$C_5$alkyl,
- $V_1$ is a $C_1$–$C_4$alkylene radical,
- $m_1$ is 0, 1 or 2,
- t is 1 to 5, and
- $R_6$ is hydrogen or $C_1$–$C_5$alkyl.

7. A liposomogenic UV absorber according to claim 1, wherein the UV chromophore ($Q_2$) is derived from a triazine compound of the formula (6)

in which
- $R_{14}$ and $R_{15}$, independently of one another, are hydrogen, hydroxyl, $C_1$–$C_5$alkyl or $C_1$–$C_5$alkoxy.

8. A liposomogenic UV absorber according to claim 1, wherein the UV chromophore ($Q_3$) is derived from a benzotriazole compound of the formula (7)

in which
- $R_{16}$ and $R_{18}$, independently of one another, are hydrogen, $C_1$–$C_{18}$alkyl or $C_1$–$C_8$alkoxy which is unsubstituted or substituted by phenyl, or halogen or the group $$-CH_2-N\begin{matrix}R_{19}\\CO-(O)_{t_2-1}-R_{20}\end{matrix}\qquad(7a)$$

in which

R$_{19}$ is hydrogen, C$_1$–C$_{10}$alkyl, C$_5$–C$_8$cycloalkyl, C$_7$–C$_{10}$aralkyl or C$_6$–C$_{10}$aryl, R$_{20}$ is hydrogen, C$_1$–C$_{20}$alkyl, C$_2$–C$_{17}$alkenyl, C$_5$–C$_8$cycloalkyl, C$_7$–C$_{10}$aralkyl or C$_6$–C$_{10}$aryl, and t$_2$ is 1 or 2, and, if t$_2$=1, R$_{19}$ and R$_{20}$, together with the ring bridge member $$-N-CO-$$

can also form a mono- or polynuclear nitrogen-containing heterocycle and in this case R$_{19}$ is —CO— or methylene which is unsubstituted or substituted by C$_1$–C$_5$alkyl and R$_{20}$ is C$_2$–C$_5$alkylene, C$_2$–C$_5$alkenylene, C$_5$–C$_{10}$arylene or vicinally bonded di-, tetra- or hexahydro-C$_6$–C$_{10}$arylene, R$_{17}$ is C$_1$–C$_{18}$alkyl, C$_1$–C$_{18}$alkoxy, halogen, C$_6$–C$_{10}$aryl, C$_7$–C$_{10}$aralkyl or C$_5$–C$_8$cycloalkyl, and the ring B can be substituted in positions 1, 2 and 3 by C$_1$–C$_5$alkyl, C$_1$–C$_5$alkoxy, carboxyl, C$_2$–C$_9$alkoxycarbonyl, H$_2$NCO—, SO$_2$—, C$_1$–C$_5$alkylsulphonyl, halogen or by the radical of the formula (7b)

9. A liposomogenic UV absorber according to claim 1, wherein the UV chromophore (Q$_4$) is derived from a benzophenone compound of the formula (9)

in which

R$_{23}$ is hydrogen, hydroxyl, C$_1$–C$_{14}$alkoxy, phenoxy or amino, where C$_1$–C$_{14}$alkoxy can be substituted by a radical of the formula (9a)

and/or an acyloxy radical,

R$_{24}$ is hydrogen, halogen or C$_1$–C$_5$alkyl,

R$_{25}$ is hydrogen, hydroxyl or C$_1$–C$_5$alkoxy, and

R$_{26}$ is hydrogen or hydroxyl.

10. A liposomogenic UV absorber according to claim 1, wherein the UV chromophore (Q$_5$) is derived from para-aminobenzoic acid derivatives of the formula (10)

in which

R$_{27}$ is hydroxyl, halogen, cyano, C$_1$–C$_5$alkyl, C$_1$–C$_5$alkoxy, mono-C$_1$–C$_5$alkylamino or di-C$_1$–C$_5$alkylamino, R$_{28}$ is hydrogen or C$_1$–C$_5$alkyl, R$_{29}$ and R$_{30}$, independently of one another, are hydrogen or C$_1$–C$_5$alkyl, and m$_2$ is 0, 1 or 2.

11. A liposomogenic UV absorber according to claim 1, wherein, as UV chromophore (Q), radicals of the formulae (6a)

or

-continued

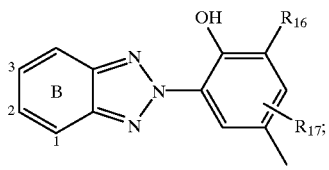
(7a)

are employed in which $R_{14}$ is hydrogen, hydroxyl, $C_1$–$C_5$alkyl or $C_1$–$C_5$alkoxy, $R_{16}$ and $R_{18}$, independently of one another, are hydrogen, $C_1$–$C_{18}$alkyl or $C_1$–$C_8$alkoxy which is unsubstituted or substituted by phenyl, or halogen or the group

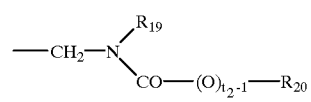
(7a')

in which $R_{19}$ is hydrogen, $C_1$–$C_{10}$alkyl, $C_5$–$C_8$cyloalkyl, $C_7$–$C_{10}$aralkyl or $C_6$–$C_{10}$aryl, $R_{20}$ is hydrogen, $C_1$–$C_{20}$alkyl, $C_2$–$C_{17}$alkenyl, $C_5$–$C_8$cycloalkyl, $C_7$–$C_{10}$aralkyl or $C_6$–$C_{10}$aryl, and $t_2$ is 1 or 2, and, if $t_2=1$, $R_{19}$ and $R_{20}$, together with the ring bridge member

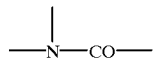

can also form a mono- or polynuclear nitrogen-containing heterocycle and in this case $R_{19}$ is —CO— or methylene which is unsubstituted or substituted by $C_1$–$C_5$alkyl and $R_{20}$ is $C_2$–$C_5$alkylene, $C_2$–$C_5$alkenylene, $C_6$–$C_{10}$arylene or vicinally bonded di-, tetra- or hexahydro-$C_6$–$C_{10}$arylene, $R_{17}$ is $C_1$–$C_{18}$alkyl, $C_1$–$C_{18}$alkoxy, halogen, $C_6$–$C_{10}$aryl, $C_7$–$C_{10}$aralkyl or $C_5$–$C_8$cycloalkyl, and the ring B is optionally substituted in positions 1, 2 and 3 by $C_1$–$C_5$alkyl, $C_1$–$C_5$alkoxy, carboxyl, $C_2$–$C_9$alkoxycarbonyl, $H_2NCO$—, $SO_2$—, $C_1$–$C_5$alkylsulphonyl, halogen or by the radical of the formula

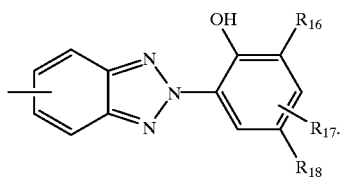
(7b)

12. A liposomogenic UV absorber according to claim 1 of the formula

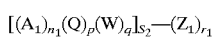
(13)

in which $A_1$ is a hydrophobic alkyl, alkoxy, acyl or alkylamino radical, the chains having at least 8 carbon atoms, Q is a UV chromophore, selected from the group consisting of
($Q_2$) triazine derivatives,
($Q_3$) benzotriazoles,
($Q_4$) benzophenones, and
($Q_5$) p-aminobenzoic acid derivatives, W is a divalent alkylene radical, $Z_1$ is a hydrophilic radical, $n_1$ is a number from 1 to 4, p is 1 or 2, q is 1 to 3, $r_1$ is 1 or 2, and $S_2$ is 1 to 3.

13. A liposomogenic UV absorber according to claim 1 of the formula

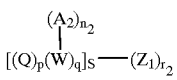
(14)

in which $A_2$ is a hydrophobic alkyl, alkoxy, acyl or alkylamino radical, the chains having at least 8 carbon atoms, Q is a UV chromophore selected from the group consisting of
($Q_2$) triazine derivatives,
($Q_3$) benzotriazoles,
($Q_4$) benzophenones, and
($Q_5$) p-aminobenzoic acid derivatives, W is a divalent alkylene radical, $Z_1$ is a hydrophilic radical, $n_2$ is 1 or 2, p is 1 or 2, q is 1 to 3, $r_2$ is 1 or 2, and s is 1 or 2.

14. A cosmetic composition comprising 0.1 to 15% by weight of a liposomogenic UV absorber of the formula

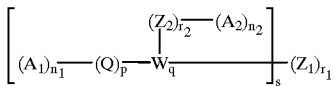
(1)

in which $A_1$ and $A_2$, independently of one another, are a hydrophobic alkyl, alkoxy, acyl or alkylamino radical, the chains having at least 8 carbon atoms, Q is a UV chromophore selected from the group consisting of
($Q_1$) cinnamic acid esters,
($Q_2$) triazine derivatives,
($Q_3$) benzotriazoles,
($Q_4$) benzophenones, and
($Q_5$) p-aminobenzoic acid derivatives, W is a divalent alkylene radical, $Z_1$ and $Z_2$, independently of one another, are a hydrophilic radical selected from the class of ($Z_a$) ammonium or amine compounds, ($Z_b$) phosphate compounds, ($Z_3$) carboxylate compounds, ($Z_d$) polyols, and ($Z_e$) sulphate compounds, $n_1$ and $n_2$, independently of one another, are a number from 0 to 4, $n_1=n_2=0$ not being additionally included, p is 1 or 2, q is a number from 0 to 3, $r_1$ is 1 or 2, $r_2$ is 0 or 1, and s is a number from 1 to 3; and a cosmetically tolerable excipient or auxiliary.

15. A cosmetic composition according to claim 14 which is a sunscreen composition.

* * * * *